(12) United States Patent
Richards

(10) Patent No.: US 6,667,006 B2
(45) Date of Patent: Dec. 23, 2003

(54) EMANATOR AND LAMP FOR DISPERSING VOLATILES

(75) Inventor: Victoria M. Richards, 220 Hillcrest Ridge, Canton, GA (US) 30115

(73) Assignees: Victoria M. Richards, Canton, GA (US); Randall G. Richards, Canton, GA (US)

(*) Notice: Subject to any disclaimer, the term of this patent is extended or adjusted under 35 U.S.C. 154(b) by 0 days.

(21) Appl. No.: 10/085,577

(22) Filed: Feb. 26, 2002

(65) Prior Publication Data

US 2003/0161755 A1 Aug. 28, 2003

(51) Int. Cl.⁷ .................................................. A62B 7/08
(52) U.S. Cl. ............................ 422/4; 422/5; 422/123; 422/125; 422/126
(58) Field of Search ........................... 422/4, 5, 126, 422/123, 125

(56) References Cited

U.S. PATENT DOCUMENTS

| | | | |
|---|---|---|---|
| 5,669,767 A | 9/1997 | Bureau et al. | 431/320 |
| 5,840,246 A | 11/1998 | Hammons et al. | 422/4 |
| 5,840,257 A | 11/1998 | Bureau et al. | 422/125 |
| 6,290,914 B1 | 9/2001 | LeJeune et al. | 422/125 |
| 6,333,009 B1 | 12/2001 | Allison | 422/125 |
| 6,426,051 B1 * | 7/2002 | Allison | 422/125 |

* cited by examiner

*Primary Examiner*—Krisanne Thornton
(74) *Attorney, Agent, or Firm*—George F. Helfrich; David W. Parker

(57) ABSTRACT

Disclosed is an oil lamp disperser and an oil lamp that disperses a volatile material from a fuel and volatile material mixture while the oil lamp is burning. The volatile material is released from the surface of an emanator element as the fuel and volatile material mixture passes through the emanator element prior to reaching the flame of the lamp. Proper construction of the lamp allows the lamp to volatilize substantial amounts of the volatile material into the surrounding environment.

16 Claims, 4 Drawing Sheets

EMANATOR AND LAMP FOR DISPERSING VOLATILES

CROSS-REFERENCE(S) TO RELATED APPLICATION(S)

Not applicable.

BACKGROUND OF THE INVENTION

1. Field of the Invention

The present invention relates to an oil lamp disperser and an oil lamp that disperse a volatile material as a lamp burns and more specifically to a disperser and lamp that disperse the volatile material from a mixture of fuel and volatile material whereby the volatile material is dispersed in an even manner all the while the lamp is in operation.

2. Description of the Related Art

Oil lamps have been burned using petroleum and vegetable oils for light and aesthetic purposes for centuries. Dispersing a volatile material from the lamp into the surrounding air while the lamp burns, has been a desirable feature of an oil lamp. Attempts to simultaneously disperse a volatile material and provide light from the oil lamp have resulted in complex, unsafe and unreliable devices until now.

The simple addition of a volatile material to the fuel of a conventional oil lamp does not promote the dispersion of the volatile material to the surrounding environment when the lamp is burning. This is due to the fact that the volatile material has no opportunity to be released from the fuel into the air during the operation of the lamp. The volatile material is almost completely consumed along with the fuel in the flame of the lamp as the oil lamp burns. Therefore, the addition of a volatile material to the fuel of a conventional oil lamp has been ineffective in producing a dispersion of the volatile material into the surrounding air.

One of the most common volatile materials that has been attempted to be dispersed is a fragrance. A variety of oil lamps have been described that produce fragranced air during the burning of the lamp. All of these oil lamps have significant negative drawbacks to their operation.

The use of a fragranced plastic cover for an oil lamp is described in U.S. Pat. No. 4,892,711. As the lamp heats up, fragrance is released from the cover. This device does not provide a constant, even flow of fragrance to the surroundings because the fragrance will be released less and less as the lamp burns until the fragrance in the cover is exhausted. Therefore the level of fragrance in the air is much less at the end of the life of the fragranced cover, making this device unreliable in delivering a constant level of fragrance.

The use of collars filled with fragrant oils or waxes that are placed around the lamp in the proximity of the wick have been described in U.S. Pat. No. 6,290,914. The use of a pad that is positioned around the flame to accept fragrance oils has also been described in U.S. Pat. No. 5,840,246. The use of a perfume holding area has been described in U.S. Pat. No. 5,840,257 in which fragrance is placed in a holding area around the flame of the lamp. There are several major disadvantages to all of these approaches to dispersing fragrance into the environment while burning an oil lamp. First, the collars, pad and holding area must be replaced or replenished with fragrance separately from the fuel. This is necessary because their use up rates will be very different from the use up rate of the fuel. It is likely that the collars described in the '914 patent will need to be replaced at a more frequent rate than the fuel in virtually all oil lamps. The fragrance must be replaced onto the pad and holding area described in the '246 and '257 patents frequently during the burning of the lamp for the same reason. A second major disadvantage of these devices is that the fragrance is released at a decreasing rate during the operation of the lamp. This is because there is no automatic means to replenish the fragrance as it volatilizes and leaves the collar or pad. The result is that the user smells much more fragrance when the lamp is first burning compared to after the lamp has burned for 12 hours. These devices require frequent fragrance replacement and deliver unreliable levels of fragrance to their surroundings.

U.S. Pat. Nos. 5,669,767 and 6,333,009 describe the addition of fragrance directly to the oil lamp fuel and the volatilization of the fragrance directly from the container. This is accomplished using a heat transfer system. This system transfers the heat produced by the lamp flame into the fuel/fragrance mixture within the container, heating the fuel/fragrance mixture and allowing the fragrance to escape the container through holes in the container. While these devices can fragrance the surrounding environment, they have major disadvantages. First, they produce varying fragrance levels in the air. As the lamp burns, the fuel level drops within the container. The flame, however, continues to produce the same amount of heat that is transferred into the container at the same rate with the consequence that the temperature of the fuel in the container rises as the lamp fuel is consumed. A wide temperature differential will produce widely different volatilization profiles for the fragrance as a result of different levels of fuel within the lamp. A second disadvantage of this system is that the fragrance character changes during the life of one fuel filling of the lamp. Fragrances are made with materials that have varying volatilities. Some fragrance components known as top notes are very volatile and some components known as bottom notes are not very volatile. When the lamp is first filled and the fuel/fragrance mixture heats up, the top notes of the fragrance escape rapidly through the holes in the container whereas the bottom notes escape slowly. During the initial burning of the lamp, the fragrance that is volatilized from the lamp has a high concentration of the top notes. This results in a concentration of the bottom notes in the remaining oil. During subsequent lamp burnings the fragrance that is volatilized has a higher concentration of the bottom notes. Therefore, the fragrance that is volatilized during the first half verses the last half of the lamp burn will have a very different character due to the different materials volatilized. A third disadvantage to both of the above devices that heat the lamp oil is the potential for direct user exposure to the heated lamp fuel. This exposure could occur by accidental spillage during use through the vent openings that are described that allow the volatilized fragrance to escape. This presents a safety issue due to the potential user exposure to burns from the hot fuel. Additionally, there is a great potential for damage to furniture and any other surface upon which this lamp might be placed because of the increased temperature of the container.

The invention described herein addresses and solves all of the problems described above from previous attempts to fragrance the surrounding air, by allowing the user to disperse a volatile material into the surroundings in an efficient, simple and safe means by including the volatile material directly into the fuel of the lamp for release during burning without exposing the user to the potential of direct contact with hot lamp fuel.

BRIEF SUMMARY OF THE INVENTION

Now in accordance with the invention there has been found a novel oil lamp disperser and oil lamp adapted to disperse volatile materials.

More specifically, a first embodiment of the present invention relates to a disperser having an emanator element, a fuel transfer means to transfer fuel and volatile material to the emanator element and a wick. A second embodiment of the present invention relates to an oil lamp having a container containing a fuel and a volatile material, an emanator element, a fuel transfer means to transfer the fuel and volatile material to the emanator element and a wick. In an additional embodiment a heat transfer element is adapted to transfer the heat of the lamp flame to the emanator element. In some embodiments a fragrance, insecticide or insect repellant is included in the container as the volatile material. In one embodiment icons can be included in the container. In an additional embodiment a process to treat the air comprises lighting a lamp that contains a fuel and a volatile material producing an action within the lamp to draw the fuel and volatile material through the fuel transfer means, through the emanator element where at least a portion of the volatile material volatilizes and through the wick to provide fuel to the flame, thereby producing light and volatilizing a volatile material into the surrounding air.

Further objectives and advantages of the subject invention will be apparent to those skilled in the art from the detailed description of the disclosed invention.

BRIEF DESCRIPTION OF THE SEVERAL VIEWS OF THE DRAWING(S)

DETAILED DESCRIPTION OF THE INVENTION

Figure 1:
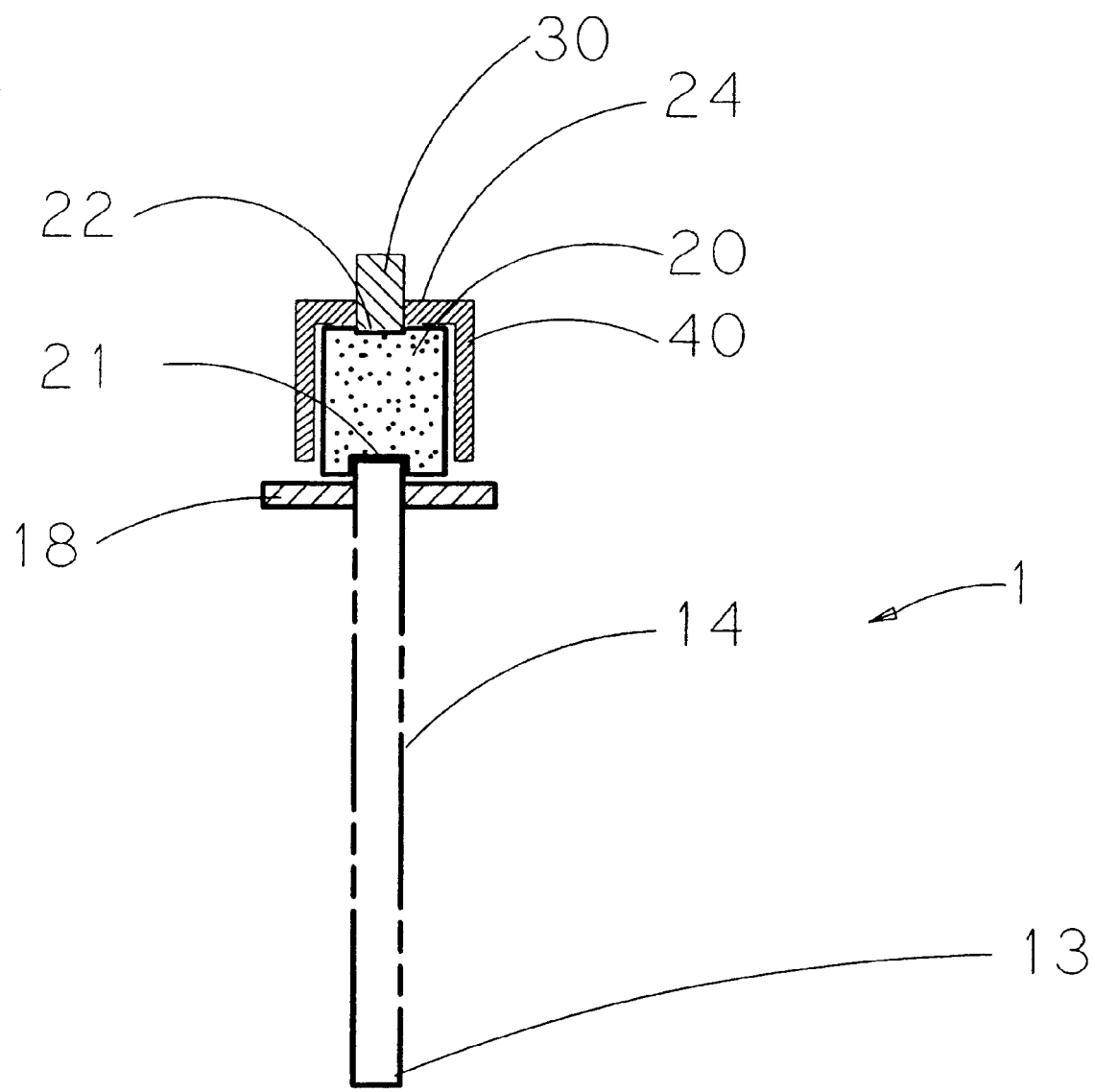
FIG. 1 shows a cross sectional view of an oil lamp disperser in accordance with the present invention.

Turning now in detail to FIG. 1 there is illustrated in cross sectional view of oil lamp disperser 1 according to the present invention. The disperser includes fluid transfer means 14, emanator element 20 and wick 30. Fluid transfer means 14 provides a system through which fuel and volatile material pass to reach the emanator element 20. Fluid transfer means holder 18 holds fluid transfer means 14 in place on the top of a container. One end 13 of fluid transfer means 14 is in contact with the fuel and volatile material. A second end 21 of fluid transfer means 14 is in direct contact with emanator element 20. Fluid transfer means 14 articulates with emanator element 20 at end 21 providing an intimate contact point where the fuel and volatile material move from fluid transfer means 14 to emanator element 20. One end 22 of wick 30 directly contacts emanator element 20 allowing fuel and volatile material to pass from emanator element 20 to wick 30. Contact points at ends 21 and 22 must provide sufficient contact between fluid transfer means 14, emanator element 20 and wick 30 to be able to provide enough fuel and volatile material to emanator element 20 to allow effective levels of volatilization of the volatile material and to provide enough fuel to wick 30 to maintain the flame. Wick 30 is held in place by heat transfer means 24. Heat transfer means 24 also functions to capture heat from the flame and transfer that heat to heat emanator 40 at a position in proximity to emanator element 20. Heat emanator 40 is designed to heat the volatile material that is present on emanator element 20 so that it will volatilize at a higher rate than it would at ambient temperature.

Figure 2:
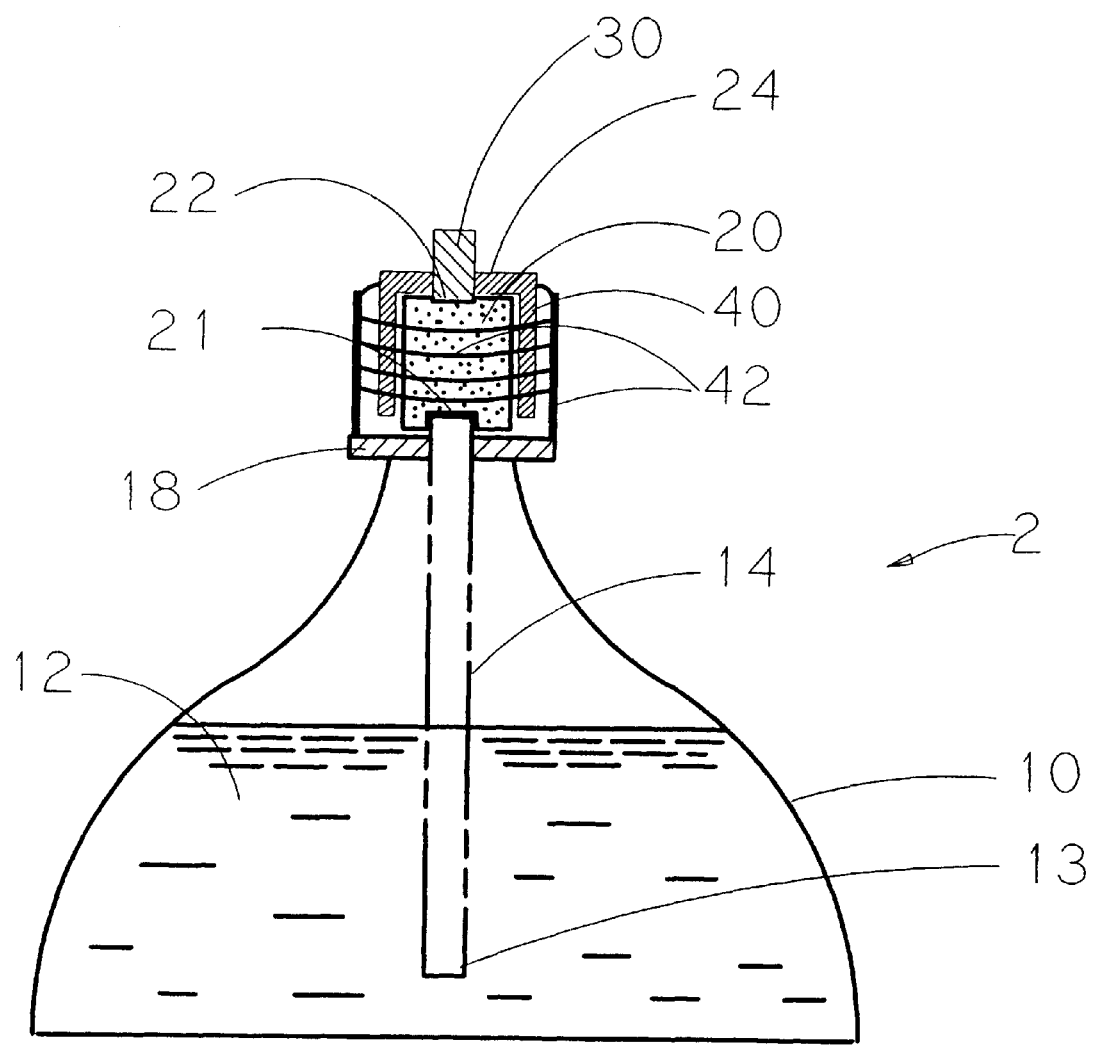
FIG. 2 shows a cross sectional view of an oil lamp in accordance with the present invention.

Turning now in detail to FIG. 2 there is illustrated in cross sectional view of oil lamp 2 according to the present invention. The lamp includes container 10 which is adapted for a quantity of fuel and volatile material 12, fluid transfer means 14, emanator element 20 and wick 30. Fluid transfer means 14 provides a system through which the fuel and volatile material pass to reach emanator element 20. Fluid transfer means holder 18 holds fluid transfer means 14 in place on the top of container 10. One end 13 of fluid transfer means 14 is in contact with the fuel and volatile material 12. A second end 21 of fluid transfer means 14 is in direct contact with emanator element 20. Fluid transfer means 14 articulates with emanator element 20 at end 21 providing an intimate contact point where the fuel and volatile material 12 move from fluid transfer means 14 to emanator element 20. One end 22 of wick 30 directly contacts emanator element 20 allowing fuel and volatile material 12 to pass from emanator element 20 to wick 30. Contact points at ends 21 and 22 must provide sufficient contact between fluid transfer means 14, emanator element 20 and wick 30 to be able to provide enough fuel and volatile material 12 to emanator element 20 to allow effective levels of volatilization of the volatile material and to provide enough fuel to wick 30 to maintain the flame. Wick 30 is held in place by heat transfer means 24. Heat transfer means 24 also functions to capture heat from the flame and transfer that heat to heat emanator 40 at a position in proximity to emanator element 20. Heat emanator 40 is designed to heat the volatile material that is present on emanator element 20 so that it will volatilize at a higher rate than it would at ambient temperature. Guard 42 is constructed to help prevent accidental contact by the user with heat transfer means 24 and heat emanator 40 and other hot surfaces.

Figure 3:
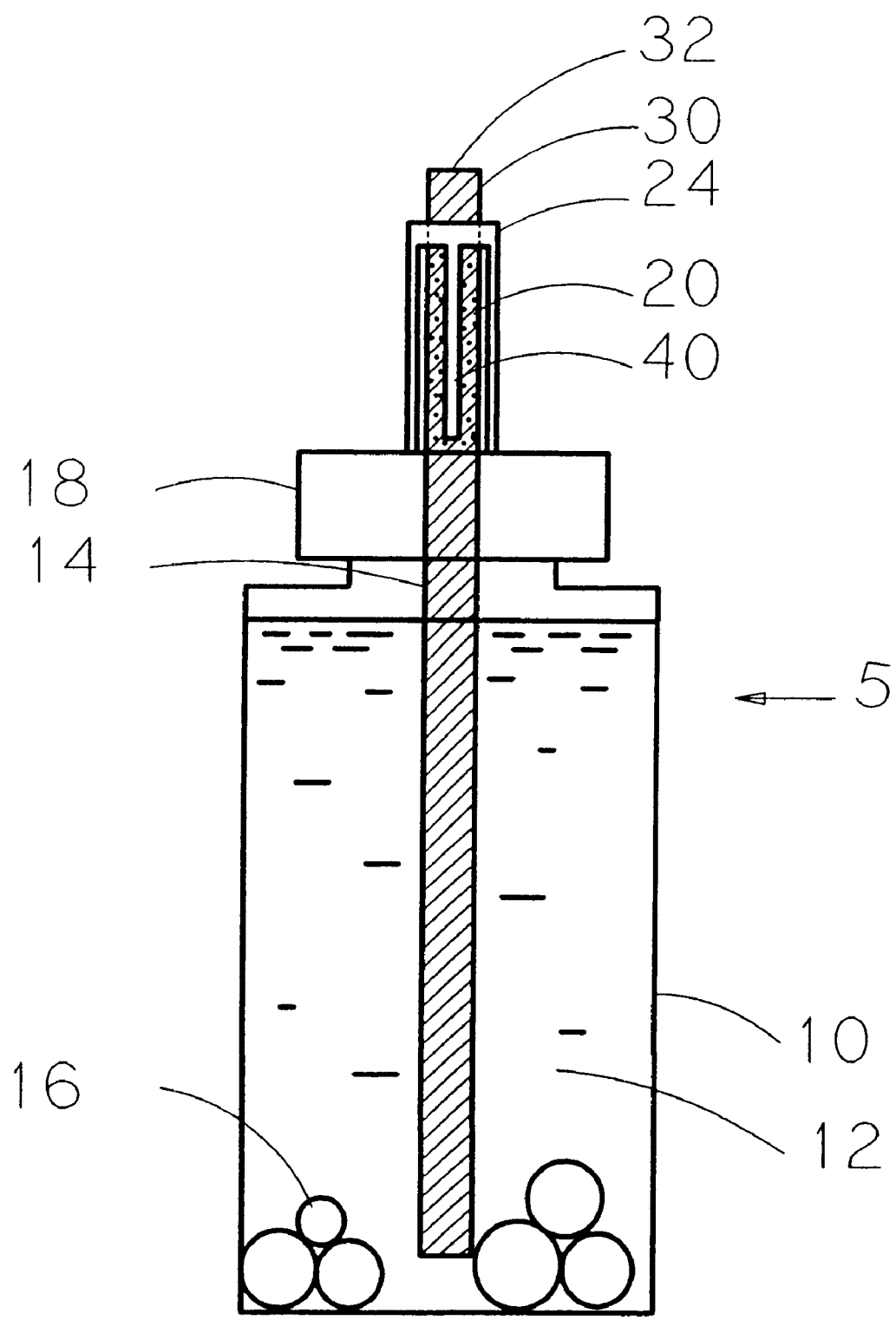
FIG. 3 shows a cross sectional view of a second embodiment of an oil lamp in accordance with the present invention.

FIG. 3 shows a cross sectional view of oil lamp 5 according to the present invention. Container 10 contains fuel and volatile material 12 and icons 16. Solid icons 16 are present primarily for aesthetic purposes although certain icons like dried fruits spices and other botanicals can add some odor to the fuel. Fluid transfer means 14 allows fuel and volatile material 12 to pass from container 10 to emanator element 20. Holder 18 holds fluid transfer means 14 and emanator element 20 and provides a cover over container 10 to prevent any accidental spillage of the fuel and volatile material 12. Emanator element 20 allows the fuel and some portion of the volatile material to pass from fluid transfer means 14 to wick 30. End 32 of wick 30 is lit during use allowing combustion of the fuel and any portion of the volatile material that does not volatilize from emanator element 20. Emanator element 20 is in proximity to heat transfer means 24 and heat transfer emanator 40. The flame present at end 32 of wick 30 heats heat transfer means 24. Heat transfer means 24 then heats the heat transfer emanator 40 which then causes increased volatilization of the volatile material. In this embodiment of the invention, fluid transfer means 14, emanator element 20 and wick 30 are continuous in construction.

Figure 4:
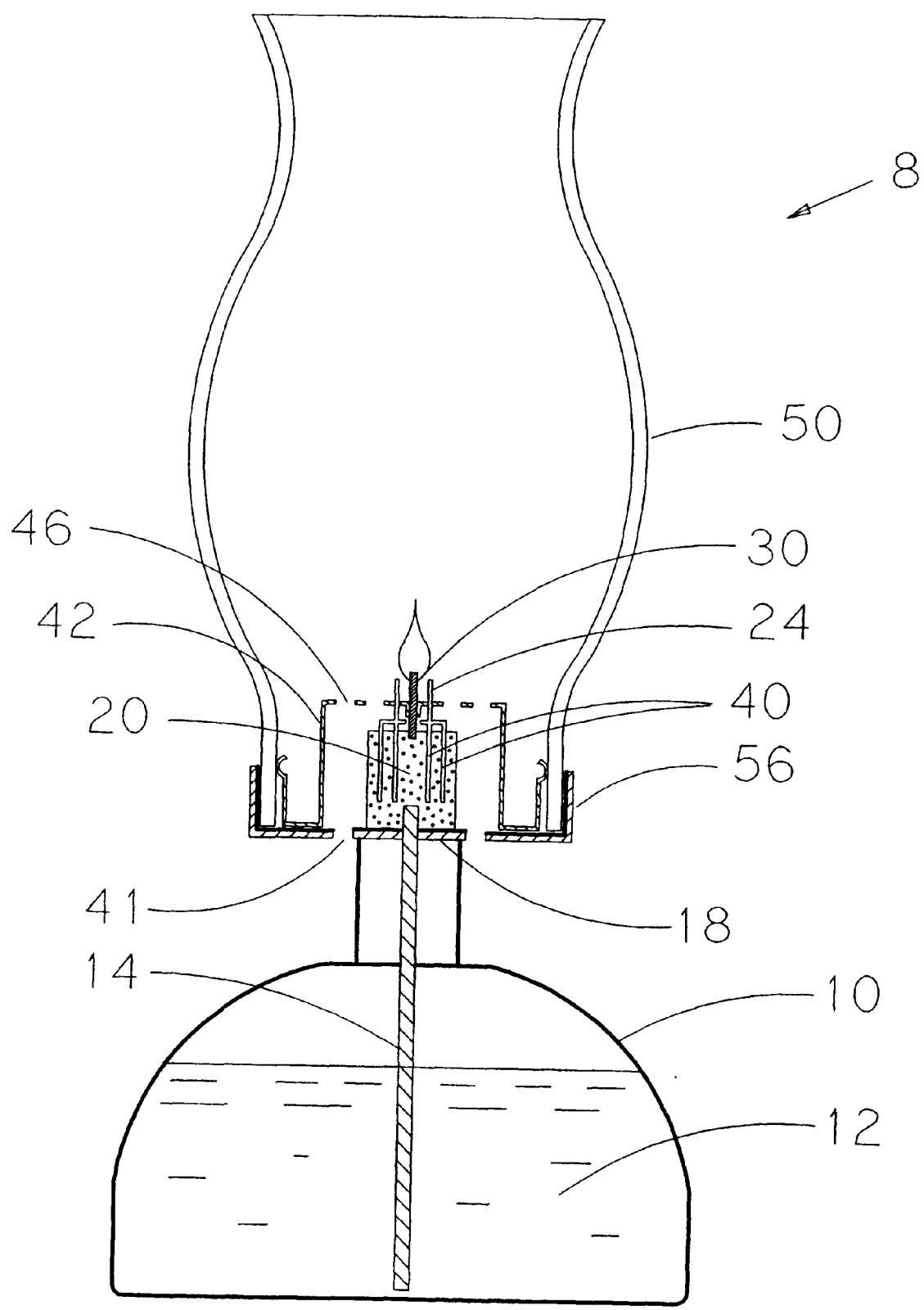
FIG. 4 shows a cross sectional view of an additional embodiment of an oil lamp in accordance with the present invention.

FIG. 4 shows a cross sectional view of oil lamp 8 according to the present invention. Container 10 contains fuel and volatile material 12 that passes through fluid transfer means 14, through emanator element 20 and is burned at wick 30. Fluid transfer means 14 and emanator element 20 are held securely in place by holder 18. The volatile material is volatilized off the surface of emanator element 20 as the fuel and volatile material mixture 12 passes through emanator element 20. Heat transfer means 24 heats up heat transfer emanator 40 which heats up emanator element 20, causing increased volitilatilization of the volatile material from emanator element 20 compared to the amount of volatilization that would occur at normal room temperature. Cover 50 protects the flame from wind currents. When wick 30 is lit, an updraft occurs that draws air through bottom vent 41, across emanator element 20 and through top vent 46 where it passes through cover 50 into the surrounding environment. When the air passes across emanator element 20 some of the volatile material volatilizes into it and is carried through top vent 46 and through cover 50 into the surrounding environment where it can be smelled.

The present invention will now be described in detail for specific preferred embodiments of the invention, it being understood that these embodiments are intended only as illustrative examples and the invention is not to be limited thereto. The present invention provides a disperser comprising (a) an emanator element from which a volatile material can volatilize, (b) a fluid transfer means having a first end that is at least partially contained within a container in contact with a fuel and volatile material, and having a second end that extends from the interior of a container to the emanator element, and (c) a wick having a first end adapted to be ignited, and a second end that contacts the emanator element. The present invention further provides an oil lamp comprising (a) a container, wherein said container contains a quantity of fuel, said fuel comprising at least one organic flammable liquid and a volatile material, (b) an emanator element from which said volatile material can volatilize, (c) a fluid transfer means having a first end that is at least partially contained within the container in contact with the fuel and volatile material, and having a second end that extends from the interior of the container to the emanator element, and (d) a wick having a first end adapted to be ignited, and a second end that contacts the emanator element. The present invention still further provides a process to disperse a volatile material into the air which includes the steps of providing a lamp having a container containing a liquid fuel and a volatile material, an emanator element, a transfer means extending between the fuel and said emanator element, igniting the wick, producing an action that draws fuel and volatile material through the emanator element to the wick, and volatilizing a portion of the volatile material from the emanator element into the surrounding air.

The fuel and volatile material that is contained within the container travels through the fluid transfer means to the emanator element. The fuel and some portion of the volatile material then travels through the emanator element to the wick where the fuel and some portion of the volatile material is combusted in the flame. As the fuel and volatile material pass through the emanator element some portion of the volatile material volatilizes into the surrounding environment. This process produces both light and a dispersion of a volatile material into the air from the lamp.

Container:

The container contains an opening through which the liquid transfer means transfers fuel and the volatile material from the container to the emanator element. The opening may include a release opening to allow return air into the container to replace the liquid that is drawn out of the container by the liquid transfer means. This release opening may be an integral part of the liquid transfer means or emanator element or may be an entirely independent release opening element. The container should have a stable base to prevent accidental tipping of the lamp.

Suitable materials of construction for the container are impervious to leakage of the fuel and volatile material and show chemical resistance to exposure to the fuel and volatile material. These materials include but are not restricted to glass, metal, ceramics and plastic with the preferred material being glass because of its clarity and chemical resistance. While the shape of the container is not critical in most instances, a preferred embodiment has an opening at or near the top of the container through which the fuel and volatile material can be transferred to the emanator element and wick.

Fuel:

The fuel that is consumed by the lamp can be any burnable organic material which has at least one liquid component at ambient or room temperature. Typical fuels can include mineral oils, paraffin oils, aliphatic hydrocarbon oils, naphthenic hydrocarbon oils, kerosene, lower hydrocarbons, alcohols, vegetable oils, surfactants, fatty acids, triglycerides, glycerides, and ethers. Because this lamp is designed to release volatile materials from the fuel, the fuel itself should possess a low odor. Fuels that contain odorants should be avoided. Preferred fuels are mineral oils, triglycerides and vegetable oils. A most preferred fuel is a highly refined mineral oil such as Conosol 260 or Drakeol 7 manufactured by Penreco of The Woodlands, Texas. The fuel may contain colorants such as oil soluble dyes or other coloring agents to improve the appearance of the fuel. An example of a suitable dye is PYLAKROME BRIGHT BLUE LX6258 manufactured by Pylam Products, Tempe, Ariz. Such fuel may also include metal salts which when burned in the flame produce a colored flame. Suitable metal salts include copper and sodium.

Icons:

Within said fuel may be placed icons of visually distinct materials. These icons may be constructed of any material that is compatible with the fuel and fragrance. The icons can also impart an olfactory effect by the inclusion of materials that leach an odiferous material into the fuel. Preferred icons are not soluble in the fuel and give a visually pleasing appearance to the fuel. Suitable icons can include glass, metals, foods, botanicals, polymeric objects, stones, sand, animal products, paper, wood and plastic. Preferred botanical icons include vegetables, fruits, candies, flowers, roots, spices, branches, and leaves. The icons may be selected so that they retain their natural appearance after they are immersed in the fuel. Botanical icons may be dried prior to immersion into the fuel.

Volatile Material:

The volatile material that is contained within the container can be a fragrance, perfume, insecticide, insect repellant, deodorizing compositions, medicinal compounds, disinfectant compositions and herbal compositions. A preferred volatile material is a fragrance. A more preferred volatile material is a fragrance with a flash point above 140° F. and most preferred with a flash point above 170° F. The volatile material is preferably compatible with the fuel that is contained in the container. A preferred embodiment includes a fuel and volatile material that are easily solubilized together or miscible, producing a stable homogeneous mixture. Two phases or separation of the fuel and volatile material is to be avoided and will lead to variability in volatile material dispersion by the lamp. A suitable fragrance is available from many commercial sources such as International Fragrance and Technology located in Canton, Ga. The preferred level of volatile material in the container comprises from about 0.01% to about 25%. A more preferred level of volatile material is from 0.5% to 5.0%. A suitable insect repellant such as DEET or Citronella oil can be included in the fuel.

Fluid Transfer Means:

The fluid transfer means provides a means for the transfer of the fuel and volatile material from the container to the emanator element. This transfer takes place at a rate that supplies enough fuel to the emanator element that can then be absorbed by the wick to produce a constant, clean burning flame. For example, if the wick is designed to consume 0.2 grams of fuel and volatile material per hour, the fluid transfer means should be sized large enough to be able to provide at least that amount of fuel and volatile material to the emanator element plus the amount of volatile material that is volatilized from the emanator element. Said fluid transfer can be accomplished a number of ways including but not limited to using capillary tubes, porous inorganic materials, porous organic materials, and reticulated polymers to carry the fuel and volatile material from the container to the emanator element.

Suitable capillary tubes that can be employed as a fluid transfer means can be constructed of glass, metal, plastic, or any other materials that are compatible with the liquid fuel and volatile material and that will allow the movement of the liquid by capillary means. The preferred material of construction for the capillary tube is glass because of its availability, chemical resistance and aesthetics. One capillary tube may provide sufficient fuel to the flame or more than one capillary tube may be needed to transfer the liquid. The capillary transfer means can be integrated into the container as an integral part of the container or incorporated into the lamp as a separate element of construction.

Suitable porous inorganic materials that can be employed as a fluid transfer means include ceramics, fritted glass, fiberglass, porcelain, stone, terra cotta, pressed metals, asbestos or other inorganic materials that contain reticulated openings or channels throughout the material's matrix. A preferred material of construction is fiberglass due to its ease of use, flexibility and high capacity to transfer a fuel and volatile material liquid. Additionally, a fiberglass transfer means tends to become transparent as it is wetted which can be aesthetically pleasing.

Suitable porous organic materials that can be employed as a liquid transfer means include cellulose materials, cotton, flax, linen, silk, paper, hemp, and wood. Because these materials have naturally occurring voids within their matrix they are suited to transfer liquids. Preferred porous organic material is cotton because of its economics and efficient transfer characteristics.

Suitable reticulated polymers for use as a liquid transfer means include nylon, polyester, rayon, polypropylene, polyurethane, polyethylene, polyamides, and rubbers. These materials may be drawn into thin strands that are woven into larger strands. These larger strands can facilitate the transfer or the fuel and volatile material liquid from the container to the emanator. These materials can also be blown using gases to produce reticulated foam that can function as a liquid transfer means.

Emanator Element:

The emanator element is designed to allow the volatilization of the volatile material from the lamp during use of the lamp. The emanator element is constructed of a material that has enough porosity to allow the fuel and volatile material to pass through the emanator element to provide sufficient fuel to the wick to maintain a constant flame, and additionally allow the volatilization of the volatile material from the surface of the emanator element as the fuel and volatile material mixture pass through it. The materials of construction of the emanator element can include organic materials, inorganic materials and polymers and combinations thereof. Suitable inorganic materials for an emanator element include inorganic porous materials such as ceramics, fritted glass, fiberglass, porcelain, stone, terra cotta, cement, clay, pressed metals, silicates, silicon oxides and other inorganic materials that are well known in the art that provide a porous structure to allow for the transfer of fuel and volatilization of a volatile material. Suitable organic materials include cellulose materials, cotton, flax, linen, silk, paper, hemp, and wood. A preferred organic emanator is treated with a fire retardant. Suitable reticulated polymers for use as an emanator element include nylon, polyester, rayon, polypropylene, polyethylene, polyamides, and rubbers. These materials can be constructed as reticulated foam and shaped into a suitable conformation to allow the transfer of fuel and the volatilization of the volatile material.

The emanator element provides a sufficient surface area and resonance time to allow the volatilization of the volatile material from the fuel and volatile material mixture as it passes through the emanator element on its way to the wick. The emanator element is constructed such that the fluid transfer means can transfer the fuel and volatile material mixture onto the emanator element.

In one preferred embodiment the emanator element is in proximity with the wick such that the heat that is generated from the flame of the lamp warms the emanator element to facilitate the volatilization of the volatile material. The wick should be positioned to prevent the flame directly contacting the emanator element due to the flammability of the fuel contained therein.

In a second preferred embodiment the wick is adjacent to a heat transfer means that can transfer the heat of the flame to the emanator element. The heat transfer means can be constructed of any material that can transfer the heat of the flame to the emanator element. A suitable material of construction for the heat transfer means is a metal. Suitable metals include copper, aluminum, steel, stainless steel, iron, nickel, chrome, brass, bronze and other metals that are good heat transfer materials. The emanator element is heated by the heat transfer means thereby causing an increase in the rate of volatilization of the volatile material of the fuel by raising the temperature of the emanator element and the fuel and volatile material mixture.

The emanator element can be enclosed within a guard to reduce the potential user exposure. Said guard can be insulated from heated portions of the invention to prevent the transfer of heat to the guard. Preferred materials for the insulation of the guard are materials that poorly conduct heat. These preferred materials of construction include plastics, ceramics, asbestos, and Bakelite. The guard can be constructed of metals or non-metals. The guard may be constructed of materials that conduct heat poorly. The guard can be constructed of a shape that protects the user from contact with hot parts of the lamp. Examples of guards are screens, crosshatched elements, and concentric rings that surround the heat transfer means and the emanator element. In a second embodiment, the guard is a solid element that prevents user contact with the hot portions of the lamp and that has openings at the top and bottom of the guard forming a chimney that allows the volatilization of the volatile material from the emanator element into the surrounding air.

Wick:

The wick is constructed to have a first end that is in contact with the emanator element and a second end that is designed to be lit. This contact point allows the fuel and a portion of the volatile material to be transferred to the wick where it is then burned in the flame. The wick can be stationary or have an adjustment means. Said adjustment means an adjust the height of the wick so that the flame height can be adjusted during use of the lamp. When the flame height is high, the flame will heat the heat transfer means allow more volatilization of the volatile material. The user may be able to extinguish the flame by retracting the wick using this adjustment means. The wick adjustment means can be similar to that found on a conventional oil lamp that is operated using a wick crank to raise or lower the wick. The construction of the wick can be of porous or woven materials that allow for the transfer of the fuel from the emanator element to the flame and that support the combustion of the fuel. Suitable wick materials include cellulose materials, cotton, flax, linen, silk, paper, hemp, wood, fiberglass, asbestos, and fritted glass. A preferred wick material is fiberglass because it is not consumed to any great extent during the combustion of the fuel.

It is possible to combine separate elements of this invention into single items of construction. For example, it is possible to combine the fuel transfer means and the emanator element into a single entity that could perform both functions of the fuel transfer means and emanator element without departing from the scope of the invention. It is also be possible to combine the wick and emanator element and liquid transfer means into a continuous element without departing from the scope of the invention. Other combinations of the elements of this disperser and lamp may also be possible without departing from the scope of the invention.

Thus, an oil lamp disperser and oil lamp that can safely, consistently and efficiently provide a significant release of a volatile material from the container of the oil lamp is now possible. Such devices are believed to have been hitherto unknown.

An advantageous feature of the oil lamp according to the invention is that the volatilization of the volatile material from the device occurs at a relatively steady rate. The burning of the lamp described herein draws a constant amount of fuel and volatile material across the emanator element. Consequently the volatilization of the volatile material from the emanator element remains relatively constant since the volatilization is directly related to the rate of fuel consumption in the present invention.

A further advantageous feature according to the invention is that the fuel and volatile material are exhausted at the same time. This relieves the user of the task of refilling the volatile material, producing component of the lamp either more or less frequently than the lamp fuel. This makes the present invention much more efficient and convenient.

A further advantageous feature according to the invention is that the character of a fragrance does not change substantially during operation of the lamp. This feature is the result of the continuous replenishing of fragrance to the emanator element from which it volatilizes. This replenishment causes the character of the fragrance that is volatilized to be very similar regardless of if the lamp has been just filled or if the lamp has almost burned all of the fuel and volatile material that was originally placed in the container.

A still further advantageous feature according to the invention is that the bulk of the lamp fuel does not have to be heated to release the volatile material in an effective manner. Since the only portion of the fuel and volatile material that is heated in the emanator element, only a very small proportion of the total fuel and volatile material is heated at any one time. Typically, only a few grams of fuel and volatile material are heated at any one time as the fuel and volatile material move through the emanator element on its way to the wick in the present invention. This advantageous feature makes the present invention described herein much less likely to pose either a fire hazard or a personal burn hazard to the user. This advantageous feature also make the present invention less likely to cause harm to any surface upon which the lamp might be placed.

EXAMPLE 1

A lamp was constructed consisting of a glass container with 300 grams of a fuel and fragrance mixture in a ratio of 97:3 respectively similar to the lamp depicted in FIG. 4. A fluid transfer means, emanator element and a wick was constructed of a continuous strip of cotton 1 inch wide and 1/16 inch thick. A heat transfer means was constructed from 2 mm round copper wire wound around the cotton strip of the emanator element. The lamp was placed in a room of approximately 1800 cubic feet. After submerging the fluid transfer means into the fuel and volatile material for 30 minutes the wick was lit. After 5 minutes of lamp operation, the fragrance was easily detected in the room.

COMPARATIVE EXAMPLE

The lamp described in Example 1 was modified to remove the emanator element and heat transfer means from the lamp. After submerging the fluid transfer means into the fuel and volatile material for 30 minutes the wick was lit. After 30 minutes of lamp operation, no fragrance could be detected in the room.

From the foregoing it will be appreciated that, although specific embodiments of the invention have been described herein for purposes of illustration, various modifications may be made without deviating from the spirit and scope of the invention. Accordingly, the invention is not limited except as by the appended claims.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

What I claim is:

1. A disperser, comprising:
   an emanator element, from which a volatile material that is mixed with a fuel is volatilized,
   a fluid transfer means having a first end that is at least partially contained within a container in contact with a mixture of a fuel and a volatile material, and having a second end that extends from the interior of the container to the emanator element, and
   a wick having a first end adapted to be ignited, and a second end that contacts with the emanator element,
   the emanator element being constructed from a porous material having a porosity sufficient to enable passage of the mixture of fuel and volatile material therethrough, and to simultaneously provide sufficient fuel to the wick to maintain a continuous flame after the wick has been ignited and to allow continuous volatilization of the volatile material from the surface of the emanator element.

2. The disperser of claim 1, which additionally comprises a heat transfer means adapted to transfer heat from the flame to the emanator element.

3. The disperser of claim 1, which is adapted for insertion into a container containing a quantity of a mixture of a fuel and a volatile material, said fuel comprising at least one organic flammable liquid.

4. A lamp, comprising;
a container, containing a quantity of a mixture of a fuel and a volatile material, said fuel comprising at least one organic flammable liquid,
an emanator element from which said volatile material is volatilized,
a fluid transfer means having a first end that is at least partially contained within the container in contact with the mixture of fuel and volatile material, and having a second end that extends from the interior of the container to contact the emanator element, and
a wick having a first end adapted to be ignited to produce a flame, and a second end that contacts the emanator element,
the emanator element being constructed from a porous material having a porosity sufficient to enable passage of the mixture of fuel and volatile material therethrough and to simultaneously provide sufficient fuel to the wick to maintain a continuous flame after the wick has been ignited and to allow continuous volatilization of the volatile material from the surface of the emanator element.

5. The lamp of claim 4 which additionally comprises a heat transfer means adapted to transfer heat from the flame to the emanator element.

6. The lamp of claim 5 wherein the heat transfer means is made of metal.

7. The lamp of claim 6 wherein the heat transfer means is made from a material selected from the group consisting of copper, aluminum, brass, tin, steel, stainless steel, zinc, chrome, nickel, iron or bronze or a combination thereof.

8. The lamp of claim 4 wherein the volatile material is a fragrance or perfume.

9. The lamp of claim 8 wherein the volatile material comprises from about 0.01% to about 25% by weight of the total fuel and volatile material contained within the container.

10. The lamp of claim 4 wherein the volatile material is an insecticide or insect repellant.

11. The lamp of claim 4 wherein the fuel is a hydrocarbon.

12. The lamp of claim 11 wherein the fuel is a mineral oil or vegetable oil.

13. The lamp of claim 4, wherein the container contains visually distinct materials which are not soluble in the mixture of fuel and volatile material and impart a visually pleasing appearance to the mixture of fuel and volatile material.

14. The lamp of claim 4 wherein the lamp contains a means to adjust the wick.

15. A process for providing a volatile material to the air which includes the steps of:
providing a lamp according to claim 1 having a container containing a liquid fuel and a volatile material, an emanator element, a transfer means extending between the fuel and said emanator element, and a wick in contact with said emanator element,
igniting the wick, to produce a flame,
producing an action that draws the fuel and volatile material through the liquid transfer means, through the emanator element, to the wick,
and volatilizing a portion of the volatile material from the emanator element into the surrounding air.

16. The process of claim 15 wherein a heat transfer means is adapted to transfer heat from the flame to the emanator element.

* * * * *